(12) United States Patent
Butler et al.

(10) Patent No.: US 8,257,721 B2
(45) Date of Patent: *Sep. 4, 2012

(54) ORAL CARE PRODUCT

(75) Inventors: Michael Francis Butler, Sharnbrook (GB); Yan Deng, Shanghai (CN); Mary Heppenstall-Butler, Sharnbrook (GB); Andrew Joiner, Wirral (GB); Haiyan Li, Bordeaux (FR); Xiaoke Li, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 52 days.

This patent is subject to a terminal disclaimer.

(21) Appl. No.: 12/517,562

(22) PCT Filed: Dec. 4, 2007

(86) PCT No.: PCT/EP2007/063252
§ 371 (c)(1),
(2), (4) Date: Jan. 27, 2010

(87) PCT Pub. No.: WO2008/068248
PCT Pub. Date: Jun. 12, 2008

(65) Prior Publication Data
US 2010/0150974 A1    Jun. 17, 2010

(30) Foreign Application Priority Data
Dec. 5, 2006    (WO) ................ PCT/CN2006/003278

(51) Int. Cl.
*A61K 8/25* (2006.01)
*A61K 8/02* (2006.01)
*A61K 8/24* (2006.01)
*A61Q 11/00* (2006.01)
*A61C 19/06* (2006.01)

(52) U.S. Cl. .................... 424/401; 424/602; 424/682

(58) Field of Classification Search .................... 424/49, 424/57; 423/335
See application file for complete search history.

(56) References Cited

U.S. PATENT DOCUMENTS

| | | | |
|---|---|---|---|
| 4,080,440 A | 3/1978 | DiGiulio et al. | |
| 4,083,955 A * | 4/1978 | Grabenstetter et al. | 424/49 |
| 4,330,519 A * | 5/1982 | Takahashi et al. | 423/335 |
| 4,612,053 A | 9/1986 | Brown et al. | |
| 4,707,504 A | 11/1987 | Walkowiak et al. | |
| 6,338,751 B1 | 1/2002 | Litkowski et al. | |
| 6,482,444 B1 | 11/2002 | Bellantone et al. | |
| 2002/0197214 A1 | 12/2002 | Bublewitz et al. | |
| 2004/0087429 A1 | 5/2004 | Ogawa et al. | |
| 2006/0018966 A1 | 1/2006 | Lin et al. | |

FOREIGN PATENT DOCUMENTS

| | | |
|---|---|---|
| CN | 1554607 | 12/2004 |
| CN | 1785862 | 6/2006 |
| WO | WO9807448 | 2/1998 |
| WO | WO2004017929 A2 | 3/2004 |
| WO | WO2005063185 A1 | 7/2005 |
| WO | 2006/052743 A1 | 5/2006 |
| WO | WO2008015117 A2 | 2/2008 |
| WO | WO2008068247 A1 | 6/2008 |
| WO | WO2008068248 A1 | 6/2008 |

OTHER PUBLICATIONS

Gaylord Chemical Company, "Dimethyl Sulfoxide (DMSO) Solubility Data". Bulletin # 102b, dated Oct. 2007.*
International Search Report PCT/EP2007/063252, Mar. 6, 2008.
Butler et al. U.S. Appl. No. 12/517,560; For: Oral Care Product; International Publication No. WO 2008/068247 A1, Jun. 12, 2008.
DMSO Dimethyl Sulfoxide (DMSO) Solubility Data, Gaylord Chemical Company LLC, Oct. 1, 2007, Bulletin #102b,.
Berggren et al., Surfactant-templated mesostructured materials from inorganic silica, Soft matter, May 27, 2005, 1, 219-226.
Dujardin et al., Bio-inspired materials Chemistry, Advanced Materials, Jun. 5, 2002, vol. 14—No. 11, 775-787, The British Library.
Hench, Biomaterials a forecast for the future, Biomaterials 1998 vol. 19 pp. 1419., 1998, 19, 1419-1423, Elsevier Science Ltd.
Hench, Bioceramics, J Am Ceram 1998 vol. 81 No. 7 pp. 1705-1708, The British Library.
Horeajada et al., Bioactivity in ordered mesoporous materials, Solid State Science, 2004, 6, 1295-1300, Elsevier.
Kokubo, Apatite Formation on Surfaces of Ceramics, metals and polymers in Body Environment, Acta Mater, Jan. 1, 1998, 46-7, 2519-2527, Elsevier Science Ltd., Great Britain.
Lopez et al., Growth of hydroxyapatite in a biocompatible mesoporous, Acta Biomaterialia, 2006, 2, 173-179, Elsevier Ltd.
Yan et al., Highly Ordered Mesoporous Bioactive glasses with Superior in Vitro Bone-Forming Bioactivities, Angew Chem Int Ed, 2004, 43, 5980-5984.
Zhao et al., Triblock Copolymer Syntheses of Mesoporous Silica with Periodic 50 to 300 Angstrom Pores, Science, Jan. 23, 1998, 279, 548-552.
DMSO Dimethyl Sulfoxide(DMSO)Solubility Data, Gaylord Chemical Company LLC, Oct. 1, 2007, Bulletin # 102b,.

* cited by examiner

*Primary Examiner* — Walter Webb
(74) *Attorney, Agent, or Firm* — Ellen Plotkin; Milton Honig

(57) ABSTRACT

An oral care product comprising a source of calcium ions, a source of phosphate ions, and an insoluble whitening agent for deposition onto the teeth, characterized in that the source of calcium ions and the source of phosphate ions are physically separate prior to the use of the product.

11 Claims, 7 Drawing Sheets

Fig.3.
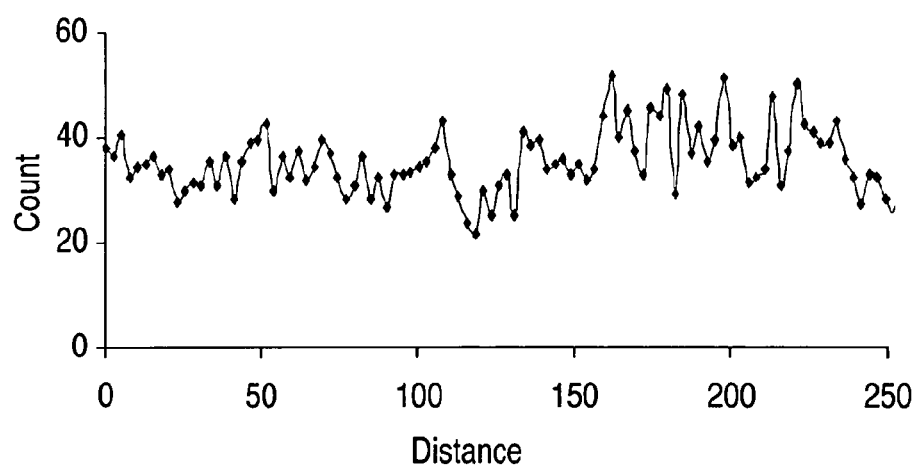
Element Ca
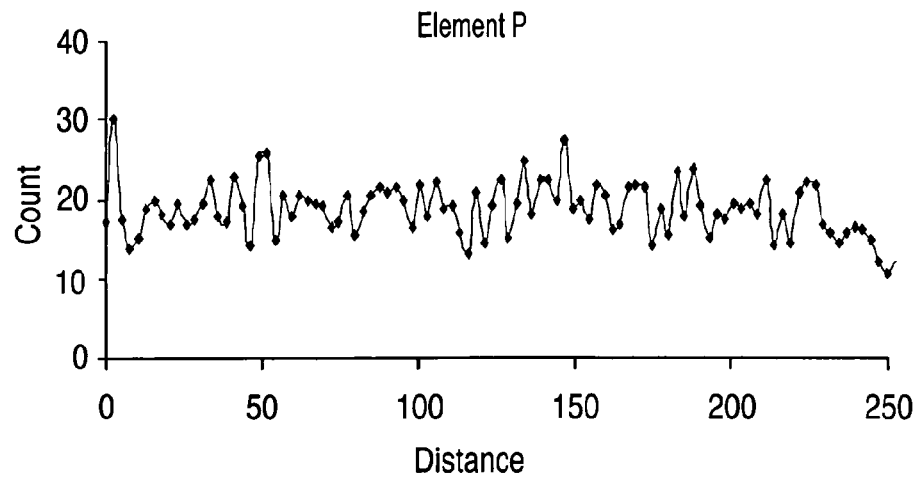
Element P

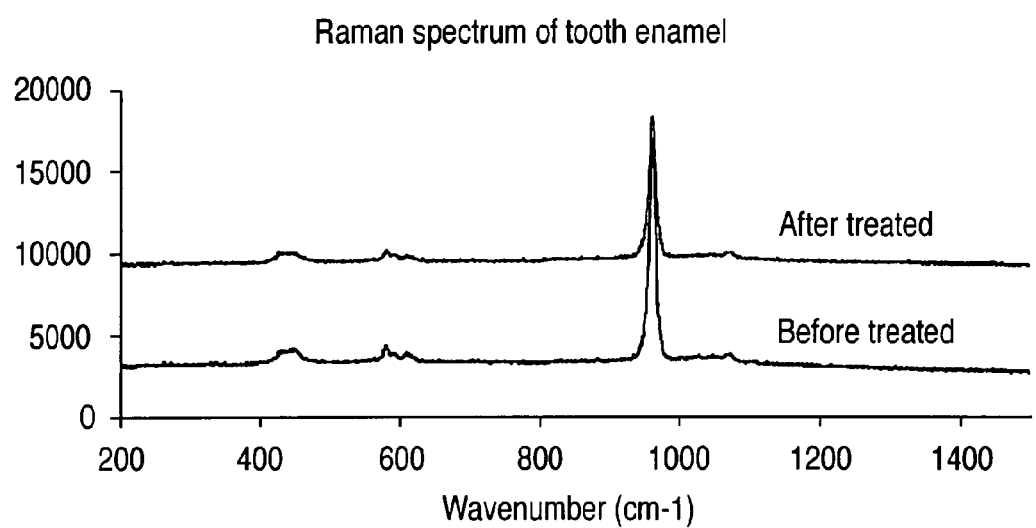

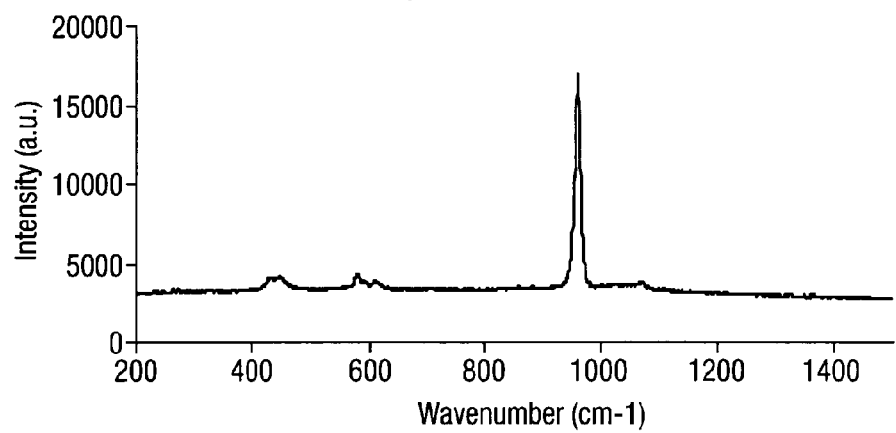
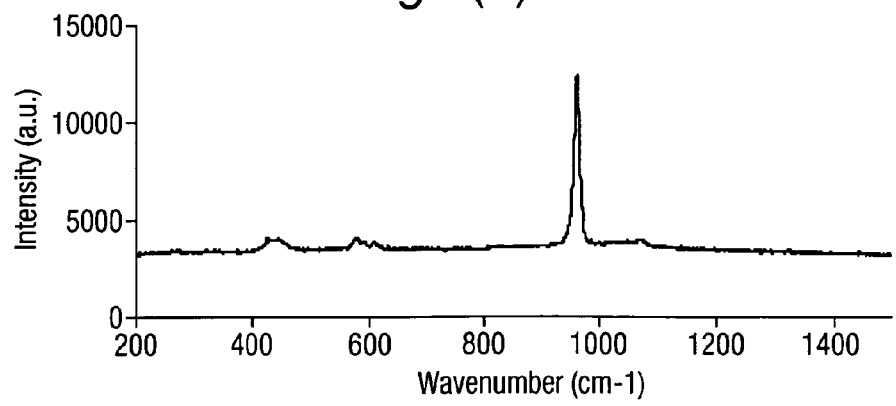

ORAL CARE PRODUCT

The present invention relates to an oral care product suitable for maintaining and/or enhancing the quality of teeth. The product comprises an insoluble whitening agent and a dual composition delivery system for said whitening agent.

The enamel layer of the tooth is naturally an opaque white or slightly off-white colour; however, this enamel layer can become stained or discoloured. The enamel layer of the tooth is composed of hydroxyapatite mineral crystals that create a somewhat porous surface. It is believed that this porous nature of the enamel layer allows staining agents and discolouring substances to permeate the enamel and discolour the tooth.

Many substances can stain or reduce the whiteness of one's teeth; in particular, certain foods, tobacco products, and fluids such as tea and coffee. These staining and discolouring substances are often able to permeate the enamel layer. This problem occurs gradually over many years, but imparts a noticeable discoloration of the enamel of one's teeth.

A variety of products are currently used for teeth whitening. Such products often comprise a peroxide compound (alone or on combination with enzymes). Such products may be used in the form of strips. Such products generally have to be removed after a well defined time, the peroxide causing damage to the teeth and/or gums if left too long. A particular problem with peroxide (and toothpastes comprising abrasive cleaners) is that it can roughen the surface of the teeth.

Certain prior art treatments are known to lead to the production of hydroxyapatite on the tooth surface.

U.S. Pat. No. 5,605,675 (Enamelon, 1997) discloses a process for remineralisation of dental enamel by application of a two-phase composition; one phase containing a water-soluble calcium compound and one phase containing a water soluble inorganic phosphate and a water-soluble fluorine compound.

U.S. Pat. No. 4,083,955 (P&G, 1978) discloses a process for remineralisation of dental enamel by sequential application of two compositions, the first comprising calcium ions and second comprising phosphate ions, or vice versa.

WO 04/017929 (Septodont ou Specialites Sepodont S.A., 2004) discloses a preparation containing: an aqueous liquid part, a solid part comprising at least one silicate selected from tricalcium silicate and dicalcium silicate; calcium chloride and a water reducing agent, to be used to restore a mineralised substance, particularly in the dental field.

An object of the present invention is to deliver an insoluble whitening agent to the surface of the teeth, whilst simultaneously enabling the production of hydroxyapatite on the surface the teeth.

The present invention involves delivering a source of calcium ions to the surface of the teeth and ultimately converting the calcium ions into hydroxyapatite in situ by the simultaneous or sequential application of a source of phosphate ions. The source of calcium ions and the source of phosphates ions are delivered from independent phases and their ability to interact prematurely is thereby minimised.

The in situ generation of hydroxyapatite results in the remineralisation of the teeth, potentially reducing the likelihood of tooth decay and improving the appearance of the teeth, in particular their whiteness, adding to the whitening effect produced by the deposition of the whitening agent. The teeth may also appear smoother and shinier as a result. Since many "whitening" treatments result in a roughening of the tooth surface, the ability to whiten and yet reduce surface roughness is a particular benefit of the present invention.

The benefits delivered by the present invention are principally targeting at the enamel; however, it is also expected that any exposed dentin may also be beneficially affected.

In a first aspect of the present invention, there is provided an oral care product comprising a source of calcium ions, a source of phosphate ions, and an insoluble whitening agent for deposition onto the teeth, characterised in that the source of calcium ions and the source of phosphate ions are physically separate prior to the use of the product.

In a second aspect of the present invention, there is provided a method of delivering an insoluble whitening agent to the teeth, said method comprising the application of the insoluble whitening agent in combination with a source or calcium ions and a source of phosphate ions, characterised in that the source of calcium ions and the source of phosphate ions are applied from physically separate compositions.

In a third aspect of the present invention, there is provided a product according to the first aspect of the invention for use as a medicament.

In a fourth aspect of the present invention, there is provided the use of:
1. a source of calcium ions;
2. a physically independent source of phosphate ions, and
3. an insoluble whitening agent for deposition onto the teeth,
in the manufacture of an oral care product for use to improve tooth whiteness, and/or reduce tooth decay, and/or reduce sensitivity.

Products according to the invention comprises an insoluble whitening agent and a dual delivery system, said dual delivery system typically comprising a first composition comprising a source of calcium ions and second composition comprising a source of phosphate ions.

The insoluble whitening agent functions by being deposited onto the teeth and thereby changing their appearance. It is believed that the deposition onto the teeth is aided by the dual delivery system, i.e. the application of calcium ions and phosphate ions from independent sources. Any insoluble whitening agent that functions in the above manner may be used.

Suitable insoluble whitening agents are particulate solids. They may comprise white particles or they may comprise blue particles; blue particles giving the teeth the appearance of increased whiteness by decreasing the "yellowness" (b*) of the teeth. The insoluble whitening agent has been found to work synergistically with the dual delivery system to deliver enhanced whitening benefits.

"Insoluble whitening particles" are insoluble in water at temperatures typically found in the oral cavity. Insoluble whitening particles typically have a solubility of less than 0.01 mol/L at 25° C.

The insoluble whitening particles preferably have an average particle size of from 200 nm to 300 nm, more preferably from 220 nm to 280 nm, and most preferably from 245 nm to 265 nm. Such particle sizes are preferred because they give the strongest light scattering of blue light (wavelength ca. 450 nm) and, as a result, the best whitening performance. Average particle size is on a number basis and may be calculated from image analysis of Scanning Electron Microscope (SEM) images taken in Secondary Electron Image (SEI) mode.

Insoluble whitening particles are preferably incorporated in the composition of which they are part at a level of from 0.01% to 5% and more preferably at from 0.03% to 2.5% by weight.

Insoluble whitening particles that are white particles are preferred, in particular titanium dioxide and zinc oxide. When used, such particles are preferably incorporated in the composition of which they are part at a level of from 0.1% to 5%, more preferably 0.25% to 3% by weight, and most preferably at from 0.5 to 2.5% by weight.

In the context of this invention, blue particles have a hue angle, h, in the CIELAB system of from 220 to 320 degrees, preferably from 250 and 290 degrees. When used, such particles are preferably incorporated in the composition of which they are part at a level of from 0.01% to 0.3%, more preferably 0.02% to 0.1% by weight, and most preferably at from 0.03 to 0.08% by weight. The blue particles are blue pigments, preferably Pigment Blue 15; more preferably Pigment Blue 15:1, 15:2, 15:3, 15:4, 15:5 or 15:6; most preferably Pigment Blue 15:1.

A preferred source of calcium ions is an insoluble calcium salt. In embodiments using such a source of calcium ions, it is believed that calcium is deposited onto the teeth before any premature interaction with phosphate in the saliva of the oral cavity can occur. Having deposited on the tooth enamel and/or dentin, slow reaction with the phosphate present in the saliva and, importantly, that added with the second composition, results in hydroxyapatite being produced exactly where it is required and aiding the deposition of the insoluble whitening agent.

Suitable insoluble calcium salts may be any salt capable of delivery to the surface of the teeth when the composition is applied, other than a calcium phosphate, which is not a source of calcium ions in accordance with this invention. Hence, calcium salts such as hydroxyapatite and fluoroapatite are not suitable insoluble calcium salts.

A preferred insoluble calcium salt is calcium silicate (CS), present as the composite material calcium oxide-silica: $CaO—SiO_2$. The use of this insoluble calcium salt is preferred because of its excellent conversion to hydroxyapatite on the tooth surface. Without wishing to be bound by theory, it is believed that the CS reacts with phosphate ions to form a calcium silicate-phosphate cement (CSPC) and that this material bonds strongly to the teeth and then gradually transforms into hydroxyapatite on the tooth surface. It is believed that the high affinity of the CSPC for the tooth surface underlies the superior remineralisation and whitening benefits obtained.

When CS is employed, its ratio of calcium to silicon (Ca:Si) may be from 1:10 to 3:1. The Ca:Si ratio is preferably from 1:5 to 2:1, more preferably from 1:3 to 1:1, and most preferably it is about 1:2. The CS may comprise mono-calcium silicate, bi-calcium silicate, or tri-calcium silicate. Higher ratios of calcium to silicate are preferred because such ratios are believed to enhance active bonding to the tooth surface and subsequent transformation into hydroxyapatite; however, lower ratios are preferred for ease of obtaining the desired pH (vide infra).

Throughout this specification, ratios of calcium to silicon (Ca:Si) should be understood to be atom ratios.

Preferably, the insoluble calcium salt is a "biomaterial", by which is meant a material that is capable of bonding to human and/or animal tissue. It is especially preferred that the biomaterial is able to bond to tooth enamel and/or tooth dentin.

"Insoluble calcium salts" are insoluble in water at temperatures typically found in the oral cavity. Insoluble calcium salts typically have a solubility of less than 0.01 mol/L at 25° C.

Suitable insoluble calcium salts may be in a crystalline or amorphous state; preferably it is in an amorphous state; more preferably it is in a mesoporous state, i.e. it is a material having pores with diameters from 1 to 50 microns. Mesoporous calcium silicate is particularly preferred and is abbreviated as MCS in this specification.

In one aspect of the invention, there is present MCS having an average pore size (diameter) of preferably from 0.4 to 4 nm, more preferably from 0.4 to 3.5 nm, and most preferably from 0.4 to 3 nm.

In another aspect of the invention, there is present MCS having an average pore size (diameter) of preferably from 2 to 4 nm, more preferably from 2 to 3.5 nm, and most preferably from 2 to 3 nm.

In a further aspect of the invention, there is present MCS having an average pore size (diameter) of preferably from 1 to 2.7 nm and more preferably from 1.35 to 2.45 nm.

The pore size may be measured using any suitable method or means. For example, the pore size may be measured using BET nitrogen sorption or mercury porosimetry techniques (particularly BET nitrogen sorption techniques).

The content of the source of calcium ions is typically from 0.05 to 25%, particularly from 0.5 to 15%, and especially from 2.5 to 10% by weight of the all the formulation components of the product as to be applied to the teeth. In terms of the specific composition of which it forms a part, the source of calcium ions is typically present at from 0.1 to 50%, particularly from 1 to 30%, and especially from 5 to 20% by weight.

Preferably, the source of calcium ions is present in a composition that is substantially free of phosphate ions. By the term "substantially free" we mean that relative to the weight of the calcium ions, the amount of phosphate ions is less than 2.5%, particularly less than 1%, more particularly less than 0.1%, and especially less than 0.01% by weight. It is possible to prepare calcium oxide-silica containing less than 0.005% by weight of phosphate ions by using high purity starting materials, for example using calcium nitride supplied by China National Pharmaceutical Group Corporation (SINOPHARM), Beijing, which has a purity of greater than 99%.

Preferably, the source of calcium ions is present in a composition that is substantially free of fluoride ions. By the term "substantially free" we mean that relative to the weight of the calcium in the insoluble calcium salt, the amount of fluoride ions is less than 2.5%, particularly less than 1%, more particularly less than 0.1%, and especially less than 0.01% by weight.

Calcium silicate suitable for use in the present invention may be prepared by the methods described in our co-pending application PCT/EP2007/057556.

The source of calcium ions is preferably present in a composition having a pH of from 7 to 11, more preferably from 8 to 10.5, and most preferably from 9 to 10. Such compositions preferably comprise an acidic buffering, such as citric acid. Such agents enable the composition to be formulated at the desired pH and are particularly desirably at higher Ca:Si ratios, for example 1:1 and greater and especially 2:1 and greater.

The source of phosphate ions used may be any source capable of delivering phosphate ions to the teeth. Preferably, the source is a water soluble salt (vide infra). Suitable water soluble salts include tri-sodium phosphate, di-sodium hydrogenphosphate, and sodium dihydrogenphosphate.

For the avoidance of doubt, the source of phosphate ions is added to the oral cavity together with the source of calcium ions. Whilst the saliva naturally present in the oral cavity provides a source of phosphate ions, this saliva should not be considered a source of phosphate ions in accordance with the present invention.

The source of phosphate ions is preferably present in a composition at a concentration of from 1 mM to 100 mM, more preferably 5 mM to 50 mM, and most preferably 10 mM to 40 mM.

Preferably, the source of phosphate ions is present in a composition that is substantially free of calcium ions. By the term "substantially free" we mean that relative to the weight of the phosphate ions, the amount of calcium ions is less than 2.5%, particularly less than 1%, more particularly less than 0.1%, and especially less than 0.01% by weight.

The source of phosphate ions is preferably present in a composition comprising a source of fluoride ions. The source may be, for example, sodium fluoride or sodium monofluorophosphate. The level of fluoride ions present may be from 200 ppm to 10,000 ppm, preferably from 1000 ppm to 4000 ppm, and more preferably from 2000 ppm to 3000 ppm. The fluoride ions, particularly at the preferred concentrations, can aid the reaction between the insoluble calcium salt and the phosphate ions added from the second composition and present in the saliva.

The source of calcium ions and the source of the phosphate ions are typically kept physically separate from one another by having them in independent compositions. The delivery of these independent compositions to the teeth may be sequential or simultaneous. In certain embodiments, for example dual phase toothpastes, the compositions are preferably delivered simultaneously.

The means of delivery may involve a dual tube having a first compartment for a first composition comprising the source of calcium ions and a second, independent compartment for a second composition comprising the source of phosphate ions. Such a dual tube typically has one of the compartments surrounding the other. Typically, the dual tube allows for co-extrusion of the two compositions.

The means of delivery may involve a single tube having first and second compositions as described above present as independent compositions within the same tube. In such embodiments, the compositions or phases are extruded from the tube as one, such extrusion being termed "contact extrusion". In such embodiments, one the compositions may be present as stripes within the other composition. In preferred embodiments, one of the compositions is present as a sheath, surrounding the other composition in the core. In particularly preferred embodiments, the core composition comprises the source of calcium ions and the sheath composition comprising a source of phosphate ions.

When two compositions are present as independent compositions within the same tube, the quantity of water within each of the compositions is preferably less than 35%, more preferably less than 30%, and most preferably less than 25% by weight. In an especially preferred embodiment of this type, the first composition has less than 20% by weight of water and the second composition has less than 25% by weight of water. It has been found that minimising the quantities of water reduces premature interaction of the calcium salt and source of phosphate ions.

In a preferred embodiment, the product according to the invention comprises a gel composition. Said gel composition preferably comprises the source or calcium ions; alternatively it may comprise the source of calcium ions. In certain embodiments, there are two independent gel compositions, the first comprising the source or calcium ions and the second comprising the source of phosphate ions. Treatment with independent gel compositions typically involves mixing of the compositions on application and leaving the mixed composition in contact with the teeth. Following such application, the mixed compositions are typically left on the teeth for from 10 minutes to 10 hours and more typically from 30 minutes to 8 hours. The application may be carried daily. The compositions may be applied from independently compartments of a dual compartment tube or from independent phases of a product contained within a single container which is typically a tube.

In certain embodiments, in particular those involving a gel composition, the means of delivery may involve a tape, in particular an adhesive tape, onto which the source of calcium ions and the source of phosphate ions are applied, prior to the strip being placed in contact with the teeth. Using this means of delivery, the compositions can be held in close contact with tooth surface, facilitating a high concentration of calcium salt and/or source of phosphate ions close to the tooth surface. Much less of the composition(s) is/are lost into the saliva using this delivery means.

Gel compositions involve the use of a gel. The gel typically comprises a polymeric matrix, and is more typically a hydrogel (vide infra). Excluding any water present, the polymeric matrix is typically present at from 1 to 25% by weight of the composition(s) of which it is a part.

In the context of this invention, a "gel" is a colloidal system in which a porous network of interconnected nano-particles spans the volume of a liquid medium. In general, gels are apparently solid, jelly-like materials. Both by weight and volume, gels are mostly liquid in composition and thus exhibit densities similar to liquids; however, they have the structural coherence of a solid.

The polymeric matrix material may be a hydrogel which, in the context of this invention, is an insoluble polymeric network containing an absorbed aqueous phase. Typically, the polymeric network is crosslinked. Typically, the content of other liquid components in the composition(s) comprising the hydrogel is not more than 10% by weight. Typically the content of water in the composition(s) comprising a hydrogel is from 80 to 99%.

Monomers used to prepare hydrogels may be selected from vinyl alcohol and acrylate, in particular sodium acrylate. Other monomers comprising an abundance of hydrophilic groups may also be used.

Preferred hydrogels comprise a polysaccharide, polyacrylamide, or polyacrylic acid.

Suitable polysaccharides may be storage polysaccharides, such as starch or glycogen, or structural polysaccharides, such as cellulose or chitin.

Suitable polysaccharides may include saccharide units selected from one or more of the following: isomaltose, glucose, fructose, galactose, xylose, mannose, sorbose, arabinose, rhamnose, fucose, maltose, sucrose, lactose, maltulose, ribose, lyxose, allose, altrose, gulose, idose, talose, trehalose, nigerose, kojibiose, and lactulose.

Preferred hydrogels comprise one or more polysaccharides selected from the group consisting of: tamarind gum, guar gum, locust bean gum, Tara, Fenugreek, Aloe, Chia, Flaxseed, Psyllium seed, quince seed, xanthan, gellan, welan, rhamsan, dextran, curdlan, pullulan, scleroglucan, schizophyllan, chitin, hydroxyalkyl cellulose, arabinan, de-branched arabinan, arabinoxylan, galactan, pectic galactan, galactomannan, glucomannan, lichenan, mannan, pachyman, rhamnogalacturonan, acacia gum, agar, alginates, carrageenan, chitosan, clavan, hyaluronic acid, heparin, inulin, cellodextrins, cellulose, and cellulose derivatives.

Particularly preferred hydrogels comprise polysaccharides selected from the group consisting of: sodium alginate, hydroxypropyl alginate, gum carrageenan, gum grabic, guar gum, karaya gum, chitosan, pectin, and starch.

Other preferred hydrogel forming components are the Carbopol polymer, which are commercially available from Noveon.

The compositions used in accordance with the invention may also comprise further ingredients which are common in the art, such as:
- antimicrobial agents, e.g. Triclosan, chlorhexidine, copper-, zinc- and stannous salts such as zinc citrate, zinc sulphate, zinc glycinate, sodium zinc citrate and stannous pyrophosphate, sanguinarine extract, metronidazole, quaternary ammonium compounds, such as cetylpyridinium chloride; bis-guanides, such as chlorhexidine digluconate, hexetidine, octenidine, alexidine; and halogenated bisphenolic compounds, such as 2,2' methylenebis-(4-chloro-6-bromophenol);
- anti-inflammatory agents such as ibuprofen, flurbiprofen, aspirin, indomethacin etc.;
- anti-caries agents such as sodium trimetaphosphate and casein
- plaque buffers such as urea, calcium lactate, calcium glycerophosphate and strontium polyacrylates;
- vitamins such as Vitamins A, C and E;
- plant extracts;
- desensitising agents, e.g. potassium citrate, potassium chloride, potassium tartrate, potassium bicarbonate, potassium oxalate, and potassium nitrate;
- anti-calculus agents, e.g. alkali-metal pyrophosphates, hypophosphite-containing polymers, organic phosphonates and phosphocitrates etc.;
- biomolecules, e.g. bacteriocins, antibodies, enzymes, etc.;
- flavours, e.g. peppermint and spearmint oils;
- proteinaceous materials such as collagen;
- preservatives;
- opacifying agents;
- colouring agents;
- pH-adjusting agents;
- sweetening agents;
- pharmaceutically acceptable carriers, e.g. starch, sucrose, water or water/alcohol systems etc.;
- surfactants, such as anionic, nonionic, cationic and zwitterionic or amphoteric surfactants;
- particulate abrasive materials such as silicas, aluminas, calcium carbonates, dicalciumphosphates, calcium pyrophosphates, hydroxyapatites, trimetaphosphates, insoluble hexametaphosphates and so on, including agglomerated particulate abrasive materials, usually in amounts between 3 and 60% by weight of the oral care composition.
- humectants such as glycerol, sorbitol, propyleneglycol, xylitol, lactitol etc.;
- binders and thickeners such as sodium carboxymethylcellulose, xanthan gum, gum arabic etc. as well as synthetic polymers such as polyacrylates and carboxyvinyl polymers such as Carbopol®;
- polymeric compounds which can enhance the delivery of active ingredients such as antimicrobial agents can also be included. Examples of such polymers are copolymers of polyvinylmethylether with maleic anhydride and other similar delivery enhancing polymers, e.g. those described in DE-A-3,942,643 (Colgate);
- buffers and salts to buffer the pH and ionic strength of the oral care composition; and
- other optional ingredients that may be included are e.g. bleaching agents such as peroxy compounds e.g. potassium peroxydiphosphate, effervescing systems such as sodium bicarbonate/citric acid systems, colour change systems, and so on.

SUMMARY OF THE FIGURES

FIG. 3 Energy Dispersive X-ray (EDX) elemental analysis of Ca and P scanned (left to right) across the dark line indicated on the SEM cross-sectional image of FIG. 2. The "distances" indicated are distances in microns.

FIG. 4 Raman spectrum of tooth surface before and after MCS-gel treatment in the presence of a phosphate containing composition.

FIG. 6*a* Raman spectrum of phosphoric acid etched tooth surface.

FIG. 6*b* Raman spectrum of phosphoric acid etched tooth surface following treatment with MCS-gel composition and phosphate containing composition for one week.

The following examples serve to illustrate the invention without limiting the invention to them. If not otherwise stated the percentages and parts are by weight.

EXAMPLES

Step I

Preparation of Gel Compositions Comprising MCS

Homogeneous suspensions of fine powder MCS (Ca:Si=1:2) in distilled water were formed in a range of concentrations from approximately 0.5% to 5%, as indicated in Table 1, using ultra-sonification. Sodium alginate gel particles were then added with vigorous stirring. After about 5 to 15 minutes, uniform white gel suspensions resulted. The pH of the gel suspensions were measured and are also indicated in Table 1.

TABLE 1

| | MCS Compositions | | | |
|---|---|---|---|---|
| | 1 | 2 | 3 | 4 |
| MSC powder (g) | 0.5 | 1.5 | 3 | 5 |
| Water (g) | 100 | 100 | 100 | 100 |
| Sodium alginate (g) | 5 | 5 | 5 | 5 |
| pH | 9.32 | 9.72 | 9.76 | 10.03 |

Further compositions were prepared as described above with the sodium alginate present at 1 g, 1.5 g, and 3 g. The viscosity of the resulting composition was found to be a function of the alginate level, being higher at the higher alginate levels.

Step II

Application of the Gel Compositions Comprising MCS

Extracted human teeth were cleaned using 75% alcohol and brushed using toothpaste to remove surface bacteria and debris. The composition designated 4 in Table 1 was uniformly painted onto the teeth at a level of 1.0 g per six teeth. The teeth were then immersed in human saliva at 37° C. After eight hours, the gel was washed off with tap water and the teeth re-immersed again in the saliva at 37° C. for the rest of day. This treatment was continued for two weeks.

The human saliva used was collected from many subjects. Its calcium concentration varied from 23 to 60 ppm and its phosphorus concentration (present as phosphate ions) varied from 124 to 154 ppm.

Figure 1A:
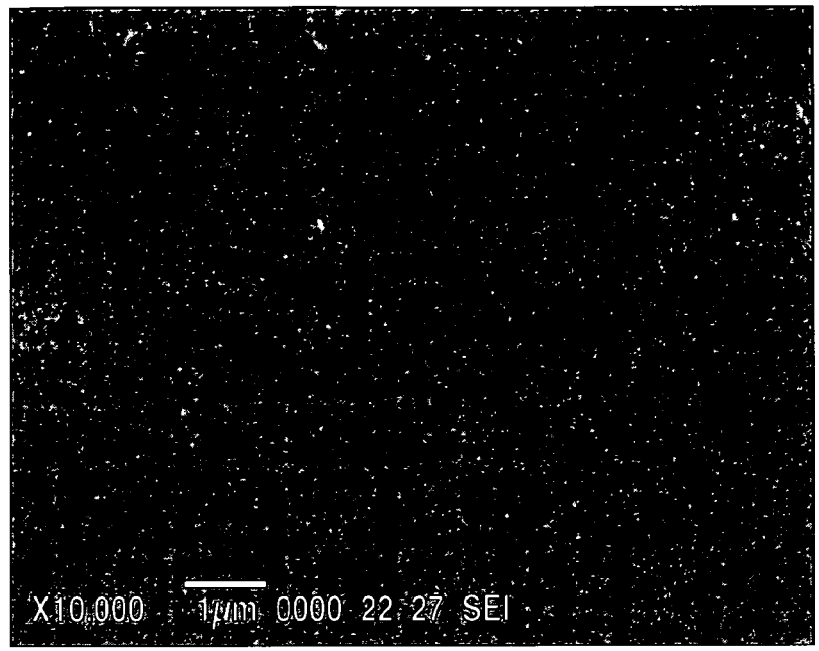
FIG. 1 Scanning electronic microscopy (SEM) image of human tooth enamel surface morphology of (a) before treatment and (b) after treatment for two weeks with MCS-gel in phosphate-containing saliva in an 8 hours/day cycling treatment.
Figure 1B:
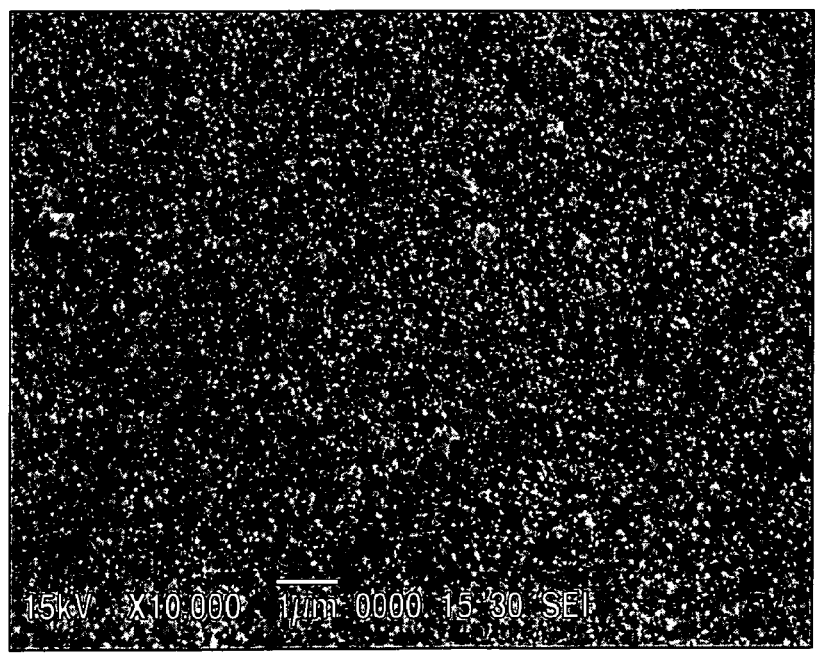

The surface morphology of the teeth was investigated using SEM before and after treatment. FIG. 1(a) represents the appearance before treatment and FIG. 1(b) represents the appearance after treatment. It can be seen that before treatment the surface is smooth and after treatment certain new crystalline structures have grown out from the original smooth surface. At a magnification of 10,000, tiny crystalline structures can be clearly seen, measuring about 100 nm.

Figure 2:
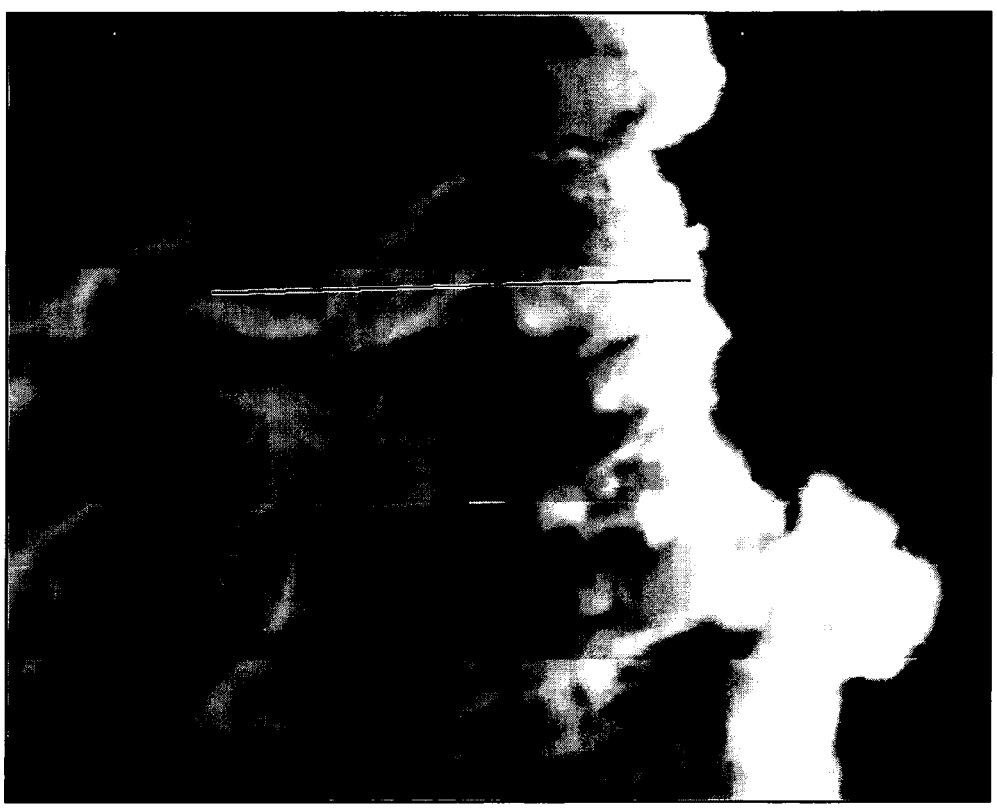
FIG. 2 SEM image of cross section view of treated tooth. A thin layer in 5 micron thickness has been formed (right bright area) on the original tooth enamel (left area).

To quantify the amount of newly formed hydroxyapatite, the before and after treatment tooth samples were sectioned and polished before being examined by SEM. The result is shown in FIG. 2. It can be clearly seen that a thin coating layer has been formed on the top of original enamel. The thickness of the layer varies from 2 to 10 microns, but seems to have a positive relation with the tooth surface roughness. Thus, it would appear that the treatment targets those teeth in most need of repair.

The chemical nature of the new crystalline material produced by the treatment was investigated by EDX elemental analysis (see FIG. 3) and Raman spectroscopy (see FIG. 4). FIG. 3 shows that the content of calcium and phosphorus in the newly formed hydroxyapatite is very similar to that in the original tooth enamel underneath. FIG. 4 indicates that the chemical nature of the phosphate present in newly formed hydroxyapatite is essentially the same as that of the untreated teeth, strongly suggesting that only "natural" hydroxyapatite has been added to the teeth.

Hardness Testing Using Nano-Indentation

In this experiment, the mechanical properties of the regenerated enamel layer were investigated. Mechanical robustness is of crucial importance to the long term stability of the enamel and is essential for maintenance of teeth during biting and eating food. It is desired that the enamel has a high level of mechanical hardness.

Using the same procedures as described in "Step II" (vide supra), human tooth samples were first cleaned and then treated with Composition 5 and phosphate-containing saliva on a daily basis for two weeks. On this occasion, however, an additional step was introduced: following the eight hour immersion of painted teeth in saliva, the teeth were brushed for one minute with a chalk-containing toothpaste. They were then re-immersed in saliva as in the "Step II" procedure described above.

State of the art nano-indentation instrumentation was used to measure the hardness of the thin film of newly deposited film of hydroxyapatite on the surface of the teeth. Three treated tooth samples were measured and on each sample, nine indentations were made. As shown in Table 3, the hardness of the remineralised layer is in the range of 5.4 and 5.7 GPa. This is very close to the hardness of the original enamel surface, also shown in Table 3. Another important mechanical parameter is Young's modulus, a basic value for a material's elasticity. The higher the value, the stiffer the material is. It is desirable that the remineralisation layer is similar to the natural enamel. From the results indicated in Table 2, it is clear that the remineralised film has similar mechanical properties that that of the original enamel.

TABLE 2 mechanical properties of teeth before and after treatment

|  | Hardness (GPa) | Young's modulus (GPa) |
|---|---|---|
| Before treatment (Literature values) | 5.0-6.0 | 95-120 |
| After forming new enamel layer | 5.4-5.7 | 111-121 |

Regeneration of Damaged Teeth

Figure 5A:
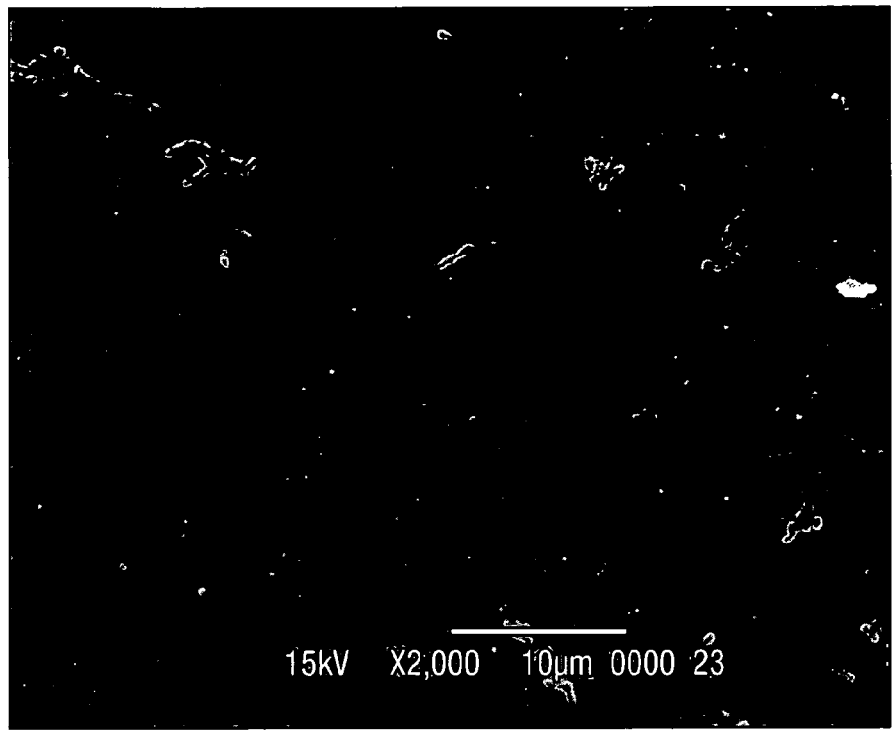
FIG. 5*a* SEM image of a tooth surface prior to "etching" with phosphoric acid.
Figure 5B:
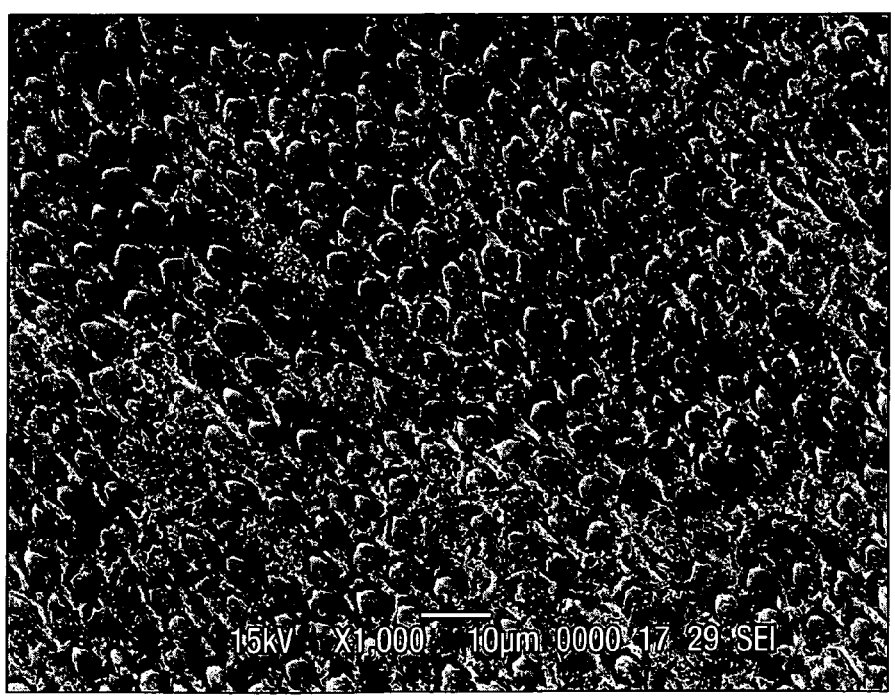
FIG. 5*b* SEM image of a tooth surface after etching with phosphoric acid.

To mimic the demineralization of teeth by many types of acidic fruit juice, human teeth were etched using 37 wt % phosphoric acid for one minute. Images of the original teeth and the phosphoric acid etched teeth were taken by SEM. FIG. 5a represents a tooth surface before etching and FIG. 5b represents a tooth surface after etching. By treatment with Composition 5 (described below) and phosphate containing saliva in the manner described above, it was found possible to cure the etching caused by the phosphoric acid within one week.

Composition 5: MCS powder (0.5 g) added to water (10 g) and dispersed as described above, then sodium alginate (0.3 g) added with vigorous stirring. A uniform gel was formed after about ten minutes stirring.

The treated samples were found to have grown a significant thickness of a new layer. The newly formed layer was characterized by Raman spectroscopy. FIG. 6a is the Raman spectrum of a tooth surface before treatment and FIG. 6b is the Raman spectrum of a tooth surface after treatment. Table 3 indicates the position of the major peaks before and after treatment. There is a peak at 961.42 cm$^{-1}$ which corresponds to the major phosphate band. The after treatment sample gave an essentially identical Raman spectrum to the before treatment sample, including the location of the phosphate band at 961.42 cm$^{-1}$. This implies that the added material is identical to that originally present and is a somewhat surprising result.

TABLE 3

Raman peaks positions of human tooth enamel before and after treatment

| Band | Position before treatment | Position after treatment |
|---|---|---|
| $v_1 PO_4^{3-}$ | 961 | 961 |
| $v_2 PO_4^{3-}$ | 445 | 444 |
| $v_3 PO_4^{3-}$ | 1072 | 1069 |
| $v_4 PO_4^{3-}$ | 579 | 579 |

The Raman bands $v_1$, $v_2$, $v_3$, and $v_4$ are characteristic of the crystallinity/perfection of the apatite crystal lattice.

Example 6

Dual Phase Gel Product

A product was prepared comprising two gel compositions: Gel I and Gel II. Details are given in Table 4. An MCS powder as described above under "step I" was incorporated into Gel I by the method disclosed under "step I". Gel II was prepared by adding sodium alginate to a solution of phosphate buffer and sodium fluoride.

TABLE 4 dual phase gel product

| | MCS Powders (wt %) | Alginate Powders (wt %) | Phosphate (mM) | Fluoride (mM) |
|---|---|---|---|---|
| Gel I | 5 | 3 | 0 | 0 |
| Gel II | 0 | 3 | 25 | 25 |

The product was applied by mixing equal weights of Gel I and Gel II and painting the mixture (total weight 2 g) onto six teeth using a cotton bud. The treated teeth were immersed in human saliva (15 ml) for one hour, at 37° C., with gentle agitation. After this time, the teeth were rinsed and cleaned using a cotton bud to remove any remaining gel. They were then placed into fresh saliva for a further two hours. This process was performed twice a day for two weeks, giving a total of 28 treatments.

In a further experiment, Example 6 as described above (i.e. a 1:1 by weight mixture of Gel I and Gel II) was applied to an adhesive plastic tape. Then the tape was then wrapped around each tooth and the wrapped teeth immersed in saliva for eight hours. The dosage applied was 2 g of the mixture of Gel I and Gel II per 6 teeth. After this time, the teeth were rinsed with water and then put into fresh saliva. This procedure was repeated for two weeks, including a tooth brushing each day to simulate real life usage.

The effects of the above treatments with Example 6, with respect to tooth whitening, were investigated together with a "control" treatment involving tooth brushing (once a day) and treatment with saliva only.

The whitening effect was measured using a Minolta Chromameter CR-321 (3 mm aperture, 45/0) to quantitatively measure the L* and b* value of each tooth before and after treatment. L* represents the overall light intensity that is reflected from the tested surface and b* represents the light contribution from the yellow-blue. Tooth whitening is indicated by an increase in reflected light intensity (L*) and a decrease in "yellowness" (b*). The results are shown in Table 5. Average colour changes after two weeks treatment are expressed as ΔL* and Δb*. Good whitening effects were observed with both treatments according to the invention.

TABLE 5

Whitening effect following treatment with Example 6

| | Application | ΔL* | ΔL* |
|---|---|---|---|
| Treatments | Painting on | 1.88 | −1.08 |
| | Strip | 4.99 | −2.24 |
| Control | Saliva only | 0.57 | −0.91 |

Examples 7-9

Dual Phase Toothpaste Products

TABLE 6

Composition details

| Component | First Composition | | | | Second Composition |
|---|---|---|---|---|---|
| | 7 | 8 | 9 | A | |
| Calcium silicate | 30 | 20 | 10 | — | — |
| FGNC[1] | 10 | 20 | 30 | 40 | — |
| NaH$_2$PO$_4$ | — | — | — | — | 6.4 |
| Na$_3$PO$_4$ | — | — | — | — | 7.6 |
| Sorbitol (70% aqu.) | 20 | 20 | 20 | 20 | 64 |
| PEG 1500 | — | — | — | — | 2 |
| Abrasive silica | — | — | — | — | 9 |
| Thickening silica | — | — | — | — | 4.8 |
| SLS[2] | 13.5 | 13.5 | 13.5 | 13.5 | — |
| SCMC[3] | 0.2 | 0.2 | 0.2 | 0.2 | 0.5 |
| Flavour | 1 | 1 | 1 | 1 | 1 |
| Saccharine | 0.3 | 0.3 | 0.3 | 0.3 | 0.3 |
| Water and minors[4] | 25 | 25 | 25 | 25 | 4.4 |

[1]Fine ground natural chalk.

[2]Sodium carboxymethylcellulose.

[3]Sodium laurylsulphate.

[4]0.25% potassium nitrate, 0.05% formaldehyde, and 0.15% triclosan in each "First Composition".

With reference to Table 6:

Example 7: 1:1 by weight mixture of First Composition 7 and the Second Composition;

Example 8: 1:1 by weight mixture of First Composition 8 and the Second Composition;

Example 9: 1:1 by weight mixture of First Composition 9 and the Second Composition;

Example A: 1:1 by weight mixture of First Composition A and the Second Composition.

These Examples were used to treat polished tooth enamel blocks. The treatment involved brushing with a slurry of the dual phase toothpaste in water (1 part toothpaste to 2 parts water) for 3 minutes, followed by incubation of the blocks in saliva for 2 hours at 37° C. This procedure was performed twice a day over a four week period. A conventional "whitening" toothpaste was used as a control, as was water.

The colour of the tooth enamel blocks was monitored using a Chromameter, as described above. The final results are indicated in Table 7, ΔL* and ΔW* representing the changes in "lightness" and "whiteness" between before and after treatment. "W" is a "whiteness measure" calculated as:

$$W = 100 - \sqrt{\{(100-L^*)^2 + a^{*2} + b^{*2}\}}$$

TABLE 7 whiteness results following use of dual phase toothpaste products

| Example used | ΔL* | ΔW* |
|---|---|---|
| 7 | 2.32 | 1.91 |
| A | 1.21 | 1.09 |

TABLE 7-continued whitening results following use of dual phase toothpaste products

| Example used | ΔL* | ΔW* |
|---|---|---|
| Toothpaste control | 0.73 | 0.36 |
| Water control | 0.56 | 0.21 |

These results indicate that Example 7 gives superior "lightening" and "whitening" in comparison with the controls.

The L* value on use of Example 7 was found to increase over time. This result is illustrated by the Figures in Table 8.

TABLE 8

Effect of duration of treatment

| | Treatment (weeks) | | | | |
|---|---|---|---|---|---|
| | 0 | 1 | 2 | 3 | 4 |
| L* | 63.52 | 64.82 | 65.37 | 65.85 | 65.84 |

The effect of the treatments on the hardness of the polished tooth enamel blocks was also investigated. This was done by measuring Knoop hardness using a HM-122 hardness testing machine (from Mitutoyo, Japan). 10 samples were measured for each treatment and 5 indentations made for each sample. The results shown in Table 9 illustrate that Examples 8 and 9 led to a significant increase ($p<0.05$) in enamel hardness.

TABLE 9 hardness results following use of dual phase toothpaste products

| | Hardness (GPa) | |
|---|---|---|
| Example used | Before | After |
| 8 | 266 | 318 |
| 9 | 276 | 333 |
| A | 281 | 271 |
| Toothpaste control | 274 | 287 |
| Water control | 296 | 283 |

The effect of the treatments on the roughness of the polished tooth enamel blocks was also investigated. This was done using a surface profilometer (SV2000 from Mitutoyo, Japan). 10 samples were measured for each treatment. The results shown in Table 10 illustrate that Examples 8 and 9 led to a significant decrease in enamel roughness, i.e., a significant increase in smoothness and shine.

TABLE 10 effect of treatments on enamel roughness

| Example used | Roughness change (%) |
|---|---|
| 8 | −10.9 |
| 9 | −10.2 |
| A | +5.2 |
| Toothpaste control | +20 |
| Water control | −2.2 |

In an independent study, the effect of the treatments upon the whiteness of whole teeth was examined. The experimental procedure was essentially the same as that described with respect to the polished tooth enamel blocks (described above), the only difference being the use of whole teeth. The results indicated in Table 11 illustrate the superior efficacy of Example 7 in comparison with a conventional whitening toothpaste.

TABLE 11 whitening results on whole teeth

| Example used | ΔL* | Δb* | ΔW* |
|---|---|---|---|
| 7 | 1.76 | −0.77 | 1.88 |
| Toothpaste control | 0.20 | −0.28 | 0.26 |

Example 10

Dual Phase Toothpaste Product

The two compositions detailed in Table 12 are intended for use in a 1:1 by weight ratio. These compositions are suitable for extrusion as independent compositions/phases from within the same compartment of the same tube, for example with the first composition forming a core and the second composition forming a surrounding sheath. The amount of water in the compositions of this Example is particularly low.

TABLE 12 dual phase toothpaste for contact extrusion

| Component | First Composition | Second Composition |
|---|---|---|
| Calcium silicate | 20 | — |
| $Na_2HPO_4$ | — | 10 |
| Sorbitol (70% aqu.) | 48 | 61 |
| PEG 1500 | 2 | 2 |
| Abrasive silica | 9 | 9 |
| Thickening silica | 8.5 | 7.5 |
| SLS | 6.6 | 6.6 |
| SCMC | 0.6 | 0.6 |
| Flavour | 1.3 | 1.3 |
| Saccharine | 0.2 | 0.2 |
| Water and minors* | 3.8 | 1.8 |

*2 ppm blue pigment in the "First Composition".

Examples 11-13

Dual Phase Gel Products

The following Examples were 50:50 by weight mixtures of the "first" composition indicated in Table 13 and each of the "second" compositions detailed in Table 13. Thus:
Example 11: first composition+second composition B;
Example 12: first composition+second composition C;
Example 13: first composition+second composition D.

TABLE 13

| | First Composition | Second Composition | | |
|---|---|---|---|---|
| Component | | B | C | D |
| Calcium silicate | 20 | — | — | — |
| $NaH_2PO_4$ | — | 10 | 10 | 10 |
| Sorbitol (70% aqu.) | 60 | 60 | 60 | 60 |

TABLE 13-continued

| Component | First Composition | Second Composition B | Second Composition C | Second Composition D |
|---|---|---|---|---|
| PEG 1500 | 2 | 2 | 2 | 2 |
| Abrasive silica | 2 | 8 | 8 | 8 |
| Thickening silica | 8 | 6 | 6 | 6 |
| SLS | 3 | 3 | 3 | 3 |
| SCMC | 0.4 | 0.8 | 0.8 | 0.8 |
| Flavour | 1 | — | — | — |
| Saccharine | 0.1 | 0.1 | 0.1 | 0.1 |
| Titanium dioxide | — | 5 | 2 | — |
| Zinc oxide | — | — | — | 2 |
| Water | 3.5 | 5.1 | 8.1 | 8.1 |

Examples 11, 12, and 13 were used to treat hydroxyapatite discs (n=6-8) for 30 minutes per day over a 4 week period. Following the 30 minute treatment, on each day, the discs were immersed in simulated oral fluid. The colour of the hydroxyapatite discs was monitored using a Chromameter, as described above. The final results are indicated at the bottom of Table 14.

TABLE 14

| Component (Levels are as applied) | Example 11 | Example 12 | Example 13 |
|---|---|---|---|
| Calcium silicate | 10 | 10 | 10 |
| Titanium dioxide | 2.5 | 1 | — |
| Zinc oxide | — | — | 1 |
| Other components | To 100 | To 100 | To 100 |
| ΔL* | 1.51 | 1.06 | 2.59 |
| Δb* | −7.53 | −2.12 | −0.79 |

These results illustrate the excellent whitening benefits that may be obtained by use of the present invention.

Examples 14-15 and Comparative Example H

These Examples were 50:50 by weight mixtures of a "first" composition and a "second" composition from Table 15. Thus:
Example 14: first composition E+second composition 14;
Example 15: first composition F+second composition 15;
Example G: first composition E+second composition G.

TABLE 15

| Component | First Composition E | First Composition F | Second Composition 14 | Second Composition 15 | Second Composition G |
|---|---|---|---|---|---|
| Calcium silicate | 30 | 20 | — | — | — |
| Potassium phosphate (1M aqu. solution) | — | — | 95 | 98 | 100 |
| FGNC | 10 | 20 | — | — | — |
| Sorbitol (70% aqu.) | 40 | 40 | — | — | — |
| SLS | 4 | 4 | — | — | — |
| SCMC | 0.5 | 0.5 | — | — | — |
| Titanium dioxide | — | — | 5 | 2 | — |
| Water | 15.5 | 15.5 | — | — | — |

Examples 14, 15, and Comparative Example G were used to treat polished hydroxyapatite discs that had been stained with black tea and coffee for 2-4 weeks at 37° C. and then brushed with water. The treatment comprised mixing the compositions and then painting onto the surface of the stained discs (n=5). The treatment was left on for 30 minutes per day over a 2 week period. Following the 30 minute treatment, on each day, the discs were rinsed with water and then immersed in simulated oral fluid. The discs were also brushed each day, to simulate real life usage.

Figure 7:
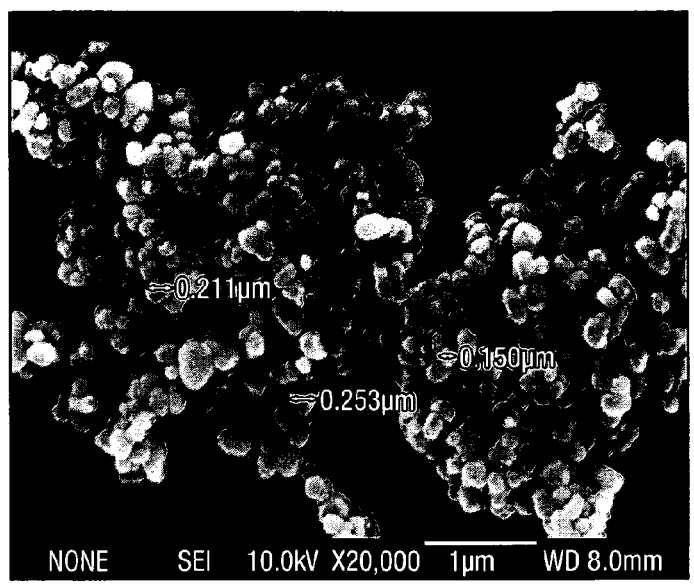
FIG. 7 SEM image of titanium dioxise raw material used in Examples 14 and 15.
Figure 8:
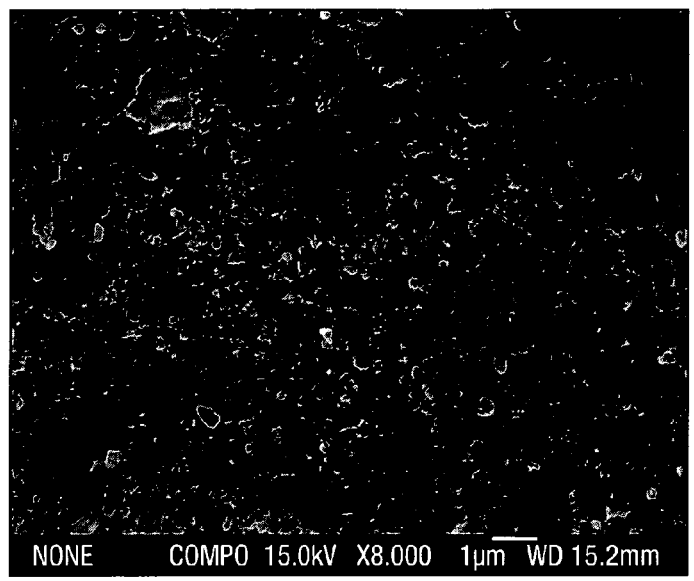
FIG. 8 SEM image HAP disc treated with Example 14.
Figure 9:
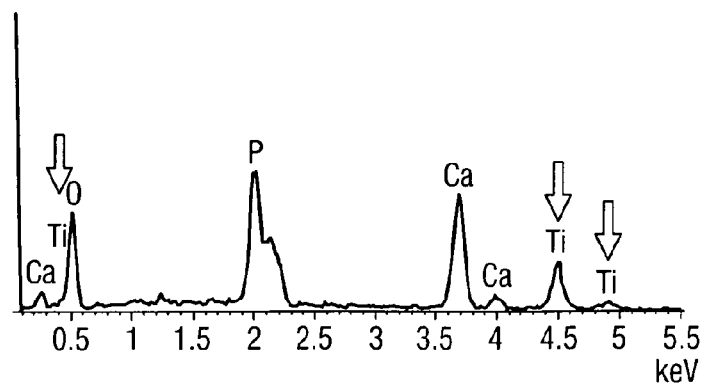
FIG. 9 Energy dispersive spectrum (EDS) of HAP disc treated with example 14.

The titanium dioxide used had an average particle size of ca. 255 nm and an SEM image of the material is shown in FIG. 7. An SEM image of the surface of a hydroxapatite disc treated with Example 14 is shown as FIG. 8. It can be seen that the titanium dioxide has been embedded in the newly formed hydroxyapatite layer and that it has maintained its morphology. FIG. 9 is an EDS spectrum of the surface of the treated disc and shows specific titanium peaks (indicated by downward arrows), further proving the incorporation of the whitening agent into the hydroxyapatite surface.

The colour of the hydroxyapatite discs was monitored using a Chromameter, as described previously. The final results are indicated at the bottom of Table 16.

TABLE 16

| Component (Levels are as applied) | Example 14 | Example 15 | Example G |
|---|---|---|---|
| Calcium silicate | 15 | 10 | 15 |
| Titanium dioxide | 2.5 | 1 | — |
| Potassium phosphate | 0.5M | 0.5M | 0.5M |
| Other components | To 100 | To 100 | To 100 |
| ΔL* | 3.15 | 1.06 | 1.03 |
| Δb* | −3.03 | −2.12 | −0.52 |

These results further illustrate the excellent whitening benefits that may be obtained by use of the present invention.

The invention claimed is:

1. An oral care product comprising a water insoluble calcium salt which is a mesoporous calcium silicate of average pore size (diameter) from 0.4 to 4 nm and having a calcium:silicon ratio of from 1:3 to 3:1, a source of phosphate ions, and a water insoluble whitening agent for deposition onto the teeth, characterised in that the mesoporous calcium silicate and the source of phosphate ions are physically separate prior to a use of the product.

2. An oral care product according to claim 1, wherein the insoluble calcium salt is present at from 0.5 to 15% by weight of the product as to be applied.

3. An oral care product according to claim 1, comprising a composition having a pH of from 8.5 to 10.

4. An oral care product according to claim 1, wherein the source of phosphate ions is a water soluble salt.

5. An oral care product according to claim 1, comprising a gel composition.

6. An oral care product according to claim 1, comprising a means of delivery involving a dual tube having a first compartment for a composition comprising the source of calcium ions and a second, independent compartment for a composition comprising the source of phosphate ions.

7. An oral care product according to claim 1, comprising a means of delivery involving a tape, onto which the source of calcium ions and the source of phosphate ions are applied, prior to the tape being placed in contact with the teeth.

8. An oral care product according to claim 1, comprising a means of delivery involving a single tube having a first composition comprising a source of calcium ions and a second, independent composition comprising a source of phosphate ions, both compositions being present within the same tube.

9. An oral care product according to claim 8, wherein the quantity of water within each of the compositions is less than 30% by weight.

10. An oral care product according to claim 9, wherein the first composition has less than 20% by weight of water and the second composition has less than 25% by weight of water.

11. An oral care product according to claim 1 which subsequent to deposition onto the teeth improves crystallinity/perfection of an apatite crystal lattice of the teeth to display Raman spectrum at bands $v_1$, $v_2$, $v_3$ and $v_4$ at respectively 961, 444, 1069 and 579 cm$^{-1}$, respectively.

* * * * *